United States Patent [19]

Reinhardt et al.

[11] 4,018,950

[45] Apr. 19, 1977

[54] DURABLE PRESS FINISHING WITH CATALYSIS BY TRIAZAPHOSPHAADAMANTANE DERIVATIVES

[75] Inventors: Robert M. Reinhardt; Donald J. Daigle, both of New Orleans; Russell M. H. Kullman, Metairie, all of La.

[73] Assignee: The United States of America as represented by the Secretary of Agriculture, Washington, D.C.

[22] Filed: Sept. 19, 1975

[21] Appl. No.: 614,994

[52] U.S. Cl. .......................... 427/381; 260/248 NS; 427/390 C; 427/394
[51] Int. Cl.$^2$ ............................................ B05D 3/02
[58] Field of Search ............. 260/248 NS; 427/381, 427/394, 390

[56] References Cited

UNITED STATES PATENTS 3,899,619   8/1975   Daigle et al. .................. 260/248 X Primary Examiner—Michael R. Lusignan
Attorney, Agent, or Firm—M. Howard Silverstein; David G. McConnell

[57] ABSTRACT

Salts of 1,3,5-triaza-7-phosphaadamantane can be utilized as catalysts for finishing cellulose-containing textile materials with methylol amide crosslinking agents to give products with improved wrinkle resistance and durable press properties. Inorganic, organic, and sulfonic acid salts, and mixed salt complexes of this new tricyclic phosphorus-containing compound provide effective catalysis in the chemical reactions needed for these finishing treatments. Salts of the corresponding phosphorus oxide, 1,3,5-triaza-7-phosphaadamantane-7-oxide, provided even stronger catalysis in similar treatments.

2 Claims, No Drawings

DURABLE PRESS FINISHING WITH CATALYSIS BY TRIAZAPHOSPHAADAMANTANE DERIVATIVES

FIELD TO WHICH INVENTION RELATES

This invention relates to catalysts for chemically finishing cellulose materials. More particularly, this invention provides novel catalysts for chemical reactions which produce improved wrinkle resistance and durable press properties in the treatment of cellulose-containing textiles with methylol amide crosslinking agents.

THE PRESENT STATE OF THE ART

The importance and economic value of wrinkle resistance and durable press properties in textile materials are well established. In fact, the majority of textile items, both wearing apparel and household articles, offered in the marketplace exhibit these properties to some useful degree. Although many synthetic fibers inherently possess resiliency and wrinkle resistance, cellulose fibers must be chemically treated to acquire these important properties needed for the modern textile market.

The principal chemical treatments which produce resiliency in cellulose are those in which the cellulose molecules are crosslinked, generally by reaction of a di- or polyfunctional agent with the cellulose. Most of the agents employed by the textile processing industry to produce wrinkle resistance in cellulosic fabrics are methylol amide adducts. For the reactions between cellulose and these adducts, acid or latent acid catalysts are required.

The state of the prior art relating to catalysts utilized in treatments for producing wrinkle resistant cellulosic textiles is presented by Marsh in chapter 9 of his monograph "Self-Smoothing Fabrics" published by Chapman and Hall Ltd. (London) in 1962, and by Reinhardt, Kullman, Furukawa, and Reid in an address before the 14th Textile Chemistry and Processing Conference, see pages 65–68 of the Proceedings published in February 1975 by the U.S. Department of Agriculture as ARS-S-60. Additional recent advances are cited in the review by D. H. Wyles "Development in the Finishing of Cotton and Man-Made-Fibre Fabrics" published by the Textile Institute in Textile Progress, volume 5, number 4, 1973.

Although many compounds and combinations of compounds have been proposed as catalysts, only a few have achieved commercial acceptance, and there has been a continuing search for better, more suitable catalysts by those concerned with the science and technology of textile chemistry. Lately, the effects of many catalysts upon health, safety, pollution, and the environment have been questioned. These factors along with the need to curtail energy consumption have prompted an increased interest in the development of new catalysts.

OBJECTS OF THE PRESENT INVENTION

It is the object of the present invention to provide new catalysts for the reactions which occur in the treatment of cellulose-containing textile materials with methylol amide crosslinking agents and which thus produce finished textiles with valuable wrinkle resistance and durable press properties. Further objects of the invention are to detail the nature of these new catalysts, their preparation, their advantages, and their use in finishing treatments.

HOW THE OBJECTS ARE ACHIEVED

The objects of this invention can be achieved with certain triazaphosphaadamantane derivatives. 1,3,5-triaza-7-phosphaadamantane is a new compound. It was first prepared and isolated by Daigle, Pepperman, and Vail, who disclosed the details in the Journal of Meterocyclic Chemistry, volume 11, pages 407–408 in June 1974. They also taught the preparation of the corresponding phosphorus oxide compound, more precisely 1,3,5-triaza-7-phosphaadamantane-7-oxide.

The structure of 1,3,5-triaza-7-phosphaadamantane has been shown to be:

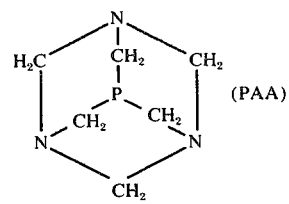

(PAA)

For convenience, this compound is hereinafter referred to as PAA. It is a unique phosphorus-containing tricyclic compound with the phosphorus atom in the P(III) form. It has the empirical formula $C_6H_{12}N_3P$ and may be considered to be a monophosphorus analog of hexamethylenetetramine.

The oxide, 1,3,5-triaza-7-phosphaadamantane-7-oxide, has the structure:

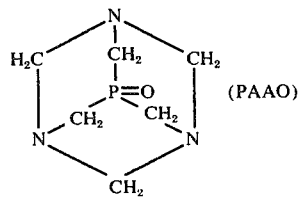

(PAAO)

It is hereinafter referred to as PAAO. In PAAO, the phosphorus atom is in the P(V) form; the empirical formula is $C_6H_{12}N_3OP$.

The chemistry of PAA and PAAO is somewhat similar to that of hexamethylenetetramine, but with some important differences. PAA and PAAO are slightly basic compounds and it has been found that salts can be prepared from these new compounds by their reactions with inorganic, organic, and sulfonic acids. The stability of PAA and PAAO salts is much greater than that of hexamethylenetetramine salts. The latter are known to be unstable in acidic solution, for example, hydrolysis to ammonia and formaldehyde is rapid in dilute hydrochloric acid, the rate being a direct function of hydrogen ion concentration (see Smolin and Rapoport, s-Triazines and Derivatives, Interscience Pub., Inc. [New York], 1959, particularly page 551). This hydrolytic decomposition is especially undesirable in any textile finishing operation, because under the conditions usually encountered during finishing, ammonia and formaldehyde can recombine to give methylamines which are the basis of offensive fishy odors that emanate from some textile products.

It has been found that salts of PAA can be utilized as catalysts for the reaction of methylol amide crosslinking agents with cellulose in finishing treatments to give textile products with improved wrinkle resistance and durable press properties. PAA salts of inorganic, organic, and sulfonic acids afford the catalysis needed for such finishing treatments. Salts of PAAO provide even stronger catalysis to yield textile products with higher levels of wrinkle resistance than those from similar treatments with the corresponding PAA salts as catalysts.

In addition, mixed salt complexes of PAA, an acid, and an inorganic salt can be prepared because of the unusual structure available in the PAA molecule. That is, in PAA, a nitrogen atom can act as a basic site while at the same time, the phosphorus functions as a nucleophile. Based upon this unusual chemical environment, recently established by Darensbourg and Daigle (see Inorganic Chemistry, volume 14, No. 5, p. 1217–1218, May 1975), mixed salt complexes, such as the PAA-glycolic acid-magnesium chloride complex, were synthesized and found to be suitable to serve as catalysts for the application of wrinkle resistance finishes to cellulose-containing textiles. The catalytic activity of such a mixed salt complex is somewhat attenuated as compared with that of the acid-inorganic salt used in combination without the PAA. This attenuation provides a means of overcoming the severe strength losses usually resulting in fabric finished with catalysis by acid-inorganic salt combinations if the strictest control of treatment conditions is not exercised during processing.

SCOPE OF THE INVENTION

Salts of PAA and PAAO which can be utilized in the process of this invention include those prepared by the reaction of these tricyclic phosphorus compounds with inorganic, organic, and sulfonic acids. These salts can be prepared and isolated as solids or prepared in solution. If isolated, they can be dissolved in water and dispensed as aqueous solutions or they can be dissolved directly in the treatment solution to be used in the textile finishing process.

Suitable salts which can serve as catalysts in finishing treatments with methylol amide crosslinking agents are the PAA and PAAO salts of inorganic acids such as HCl, HBr, Hl, $H_2SO_4$, $H_2SO_3$, $H_3PO_4$, $HClO_4$, $HBF_4$, and the like. For convenience, the salts are designated as PAA·HCl, i.e., the salt of PAA and hydrochloric acid, PAAO·HCl, PAA·HBr, etc., to avoid repeated recitation of the long precise chemical names. Salts derived from PAA or PAAO and organic acids such as glycolic acid, oxalic acid, maleic acid, malonic acid, tartaric acid, citric acid, malic acid, formic acid, chloroacetic acid, and the like, also are suitable for use as catalysts in finishing treatments with methylol amide crosslinking agents. In addition, PAA and PAAO salts of alkyl and aryl sulfonic acids, such as methanesulfonic acid, hydroxymethanesulfonic acid, propanesulfonic acid, benzenesulfonic acid, toluenesulfonic acid, and the like, are effective catalysts in such finishing treatments.

Mixed salt complexes of PAA and PAAO, which are possible due to the unusual chemical structure available in these new phosphorus derivatives, also provide catalysis suitable for finishing cellulosic textiles with methylol amide crosslinking agents. Typical of these mixed salt complexes is the PAA-glycolic acid-magnesium chloride complex. Other mixed salt complexes suitable for use as catalysts are those formed from PAA or PAAO, a Lewis acid salt, and a carboxylic acid, particularly an activated acid such as a methoxy or hydroxy-substituted carboxylic acid.

The amount of salt catalyst used may be from about 0.2 to about 6%, by weight based upon the weight of the treatment solution. The preferred range of concentrations for the salt catalysts of this invention is from about 1 to about 4%, by weight based upon the weight of the treatment solutions.

The catalysts of this invention can be used in treatments of textiles with various methylol amide crosslinking agents. These agents include formaldehyde adducts and modified formaldehyde adducts, of urea, cyclic ureas, uron, carbamates, and triazines. Typical of these agents are dimethylol urea, partially methylolated urea, methylated urea-formaldehyde, dimethylol ethyleneurea, dimethylol dihydroxyethyleneurea, dimethylol propyleneurea, dimethylol substituted propyleneurea, tetramethylol acetylenediurea, bis(methoxymethyl) uron, dimethylol methyl carbamate, dimethylol ethyl carbamate, dimethylol methoxyethyl carbamate, trimethylol melamine, methylated trimethylol melamine, partially methylated hexamethylol melamine, and the like. The amount of agent used may be from about 1 to about 25%, by weight based upon the weight of the treatment solution; the preferred range is from about 5 to 20%.

Additives, softeners, hand modifiers, wetting agents, and other components customarily included in textile finishing pad baths can be used with the catalysts of this invention. The composition of the bath is limited only by the compatibility of these ingredients with the catalyst.

The textile materials chemically finished by treatments with the catalysts of this invention may be in the form of fibers, yarns, or fabrics. The latter may be woven, knitted, or nonwoven structures. The material may be composed entirely of cellulosic fibers, either natural or regenerated, or may be composed of said cellulosics as components of the textile structure with other cellulosic, noncellulosic natural or synthetic fibers.

Conventional finishing methods are employed with the catalysts of this invention. Most common of conventional methods is the pad-dry-cure finishing process. As the name denotes, the sequence of processing steps consists of impregnating the textile material by immersing it in the treatment solution (pad bath), squeezing free of excess solution by passing through pad rolls, drying at a moderately elevated temperature (usually so that the temperature of the fabric does not exceed about 100° C), and curing at a higher temperature, generally in the range of about 140°–200° C for from about 15 seconds to about 3 minutes, time and temperature being inversely adjusted. The exact conditions of processing that are required, of course, vary with the equipment used and the material being treated.

After curing, the finished material is suitable for utilization in end products for which the textile was designed. However, it is good practice to remove unreacted chemicals and byproducts from the finished material by washing.

SUMMARY OF THE INVENTION

In summary, it may be stated that this invention encompasses the preparation of new chemical species—salts and mixed salt complexes of PAA and PAAO—and the use of these salts and complexes as novel catalysts for the reaction of methylol amide crosslinking agents with cellulose in finishing treatments of cellulose-containing textile materials to produce textile products with improved wrinkle resistance and durable press properties.

DESCRIPTION OF SPECIFIC EMBODIMENTS

The following examples further describe the invention. They are given merely as illustrations and should not be considered as limiting the scope of the invention.

In the examples, percentages reported in compositions and formulations are given as percentages by weight. Temperatures are given in degrees centigrade. Properties of the fabrics were determined by standard test methods: breaking strengths by ASTM D1682-64 (American Society for Testing and Materials); wrinkle recovery angles by AATCC Test Method 66-1968 (American Association of Textile Chemists and Colorists); durable press (DP) ratings after machine washing and tumble drying by AATCC Test Method 124-1968, procedure III-B. Nitrogen analyses of treated fabrics were by the Kjeldahl method. Analyses of chemical compounds were carried out by recognized microanalytical quantitative techniques.

EXAMPLE 1

Preparation of
1,3,5-triaza-7-phosphaadamantane-oxalic acid salt
(PAA·oxalic acid).

Aqueous solutions (20 ml each) containing PAA (3.14 g. 0.02 mole) and oxalic acid (1.8 g. 0.02 mole) were mixed together and allowed to stand at room temperature for 15 hours. The resulting precipitate was filtered and dried to yield 2.0 g (40% yield) of the PAA·oxalic acid salt.

Analysis: Calculated for $C_8H_{14}N_3O_4P$: C, 38.87%; H, 5.71%; N, 17.00%; P, 12.53%. Found: C, 38.71%; H, 5.64%; N, 16.98%; P, 12.61%.

Evaporation of the mother liquor to one-tenth volume increased the yield of salt to 95%.

EXAMPLE 2

Preparation of
1,3,5-triaza-7-phosphaadamantane-7-oxide-oxalic acid
salt (PAAO·oxalic acid)

Aqueous solutions (20 ml each) containing PAAO (3.46 g, 0.02 mole) and oxalic acid (1.8 g, 0.02 mole) were mixed together and allowed to stand at room temperature for 15 hours. The resulting precipitate was filtered and dried to yield 2.0 g (38% yield) of the PAAO·oxalic acid salt.

Analysis: Calculated for $C_8H_{14}N_3O_5P$: C, 36.51%; H, 5.36%; N, 15.97%; P, 11.77%. Found: C, 36.35%; H, 5.41%; N, 15.85%; P, 11.82%.

Evaporation of the mother liquor to one-tenth volume increased the yield of the salt to 95%.

EXAMPLE 3

PAA (0.1 g) was dissolved in 0.5 ml of 20% DCl and the solution monitored in a n.m.r. spectrometer. The spectra not change over a 24 hour period. The quantities present were $2.67 \times 10^{-3}$ mole of acid and $6.36 \times 10^{-4}$ mole of PAA which represent slightly greater than a 3 molar excess of acid.

Similarly, the n.m.r. spectra of a solution of 0.1 g PAAO in 0.5 ml of DCl was unchanged after 24 hours. The quantities present were $2.67 \times 10^{-3}$ mole of acid and $5.77 \times 10^{-4}$ mole of PAAO which represent slightly greater than a 3.5 molar excess of acid.

This example demonstrates the stabilities of these new compounds and can be contrasted with the known instability of hexamethylenetetramine in acid solutions, see Smolin and Rapoport, op. cit., p. 551.

EXAMPLE 4

Two aqueous solutions of 100 g each were prepared: one contained 9 g of dimethylol dihydroxyethyleneurea (hereinafter referred to as DMDHEU, for convenience) and 1.94 g of PAA·HCl; the other contained 9g of DMDHEU and 1.77 g of hexamethylenetetramine hydrochloride (HEX·HCl). These are equimolar amounts of PAA·HCl and HEX·HCl which were used as catalysts. Swatches of 80×80 cotton printcloth were immersed in the solutions and padded to about 75% wet pickup (i.e., 100 parts of fabric picked up 75 parts of the treatment solution, by weight), mounted on pin frames, dried at 60° C for 7 min. in an oven with mechanically circulating air, cured at 160° C for 3 min. in a similar oven, and washed. Evaluation of the properties of the finished fabrics and of an untreated control are shown in Table I.

Table 1

| Catalyst Used | DP Rating | Brk. Str.(W),lb. |
| --- | --- | --- |
| PAA . HCl | 3.2 | 35.5 |
| HEX . HCl | 2.9 | 36.3 |
| None (Untreated) | 1.0 | 48.3 |

This example demonstrates that PAA·HCl is superior to HEX·HCl as a catalyst for producing durable press properties in cotton fabric by treatment with a methylol amide crosslinking agent. Furthermore, because of the greater stability of PAA, its use in catalysis avoids the hazard of the development of fishy odors in the finished fabric.

EXAMPLE 5

Two aqueous solutions of 100 g each were prepared: one contained 9 g of DMDHEU and 2.1 g of PAAO·HCl; the other contained 9 g of DMDHEU and 2.03 g of $MgCl_2·6H_2O$. These are equimolar amounts of PAAO·HCl and $MgCl_2$ which were used as catalysts. Swatches of 80×80 cotton printcloth were treated with these solutions by the same procedure as described in Example 4. Results are shown in Table II.

Table II

| Catalyst Used | Wrinkle Recovery angle (W+F),deg. | Brk. Str. (W), lb. |
| --- | --- | --- |
| PAAO . HCl | 278 | 28.7 |
| $MgCl_2$ | 277 | 24.7 |

This example demonstrates that PAAO·HCl is equal to $MgCl_2$ (which is one of the most widely used catalysts for durable press finishing by the textile industry) in producing wrinkle resistance in a cotton fabric. Further, at the same level of wrinkle recovery, the strength of the fabric finished with PAAO·HCl as catalyst was 16% greater than that of the fabric finished with $MgCl_2$ as catalyst.

EXAMPLE 6

Three aqueous solutions of 100 g each were prepared: one contained 9 g of DMDHEU and 2.47 g of PAA·oxalic acid; another contained 9 g of DMDHEU and 2.63 g of PAAO·oxalic acid; and the third contained 9 g of DMDHEU and 0.9 g of oxalic acid. These are equimolar amounts of PAA·oxalic acid, PAAO·oxalic acid, and oxalic acid which were used as catalysts. Swatches of 80×80 cotton printcloth were treated with these solutions by the same procedure as described in Example 4. Results are shown in Table III.

Table III

| Catalyst Used | % N | Wrinkle Recovery Angle (W+F) | DP Rating | Brk. Str. (W), lb. |
|---|---|---|---|---|
| PAA . oxalic acid | 1.19 | 252 | 3.2 | 33.9 |
| PAAO . oxalic acid | 1.22 | 274 | 3.6 | 30.0 |
| Oxalic acid | 1.05 | 279 | — | 19.5 |

This example demonstrates that PAAO·oxalic acid is equal to oxalic acid in producing wrinkle resistance in a cotton fabric. Importantly, it also shows that at essentially the same level of wrinkle recovery, the strength of fabric finished with PAAO·oxalic acid as catalyst was 54% greater than that of the fabric finished with oxalic acid as catalyst. The example also shows that PAAO·oxalic acid is a more effective catalyst for producing improved wrinkle resistance and durable press properties than PAA·oxalic acid.

EXAMPLE 7

Two aqueous solutions of 100 g each were prepared: one contained 9 g of DMDHEU and 3.28 g of PAA-glycolic acid-$MgCl_2$ mixed salt complex; the other contained 9 g of DMDHEU, 0.76 g of glycolic acid, and 0.95 g of $MgCl_2$. These are equimolar amounts of the mixed salt complex and of glycolic acid and $MgCl_2$. Swatches of 80×80 cotton printcloth were treated with these solutions by the same procedure as described in Example 4. Results are shown in Table IV.

Table IV

| Catalyst Used | % N | Wrinkle Recovery Angle (W+F), deg. | Brk. Str. (W), lb. |
|---|---|---|---|
| PAA-glycolic acid $MgCl_2$ complex | 1.04 | 255 | 32.2 |
| Glycolic acid + $MgCl_2$ | 1.07 | 285 | 12.9 |

This example demonstrates that the PAA-glycolic acid-$MgCl_2$ mixed salt complex is an effective catalyst for producing improved wrinkle resistance in cotton fabric. Although not as strong a catalyst as a combination of glycolic acid and $MgCl_2$, it can be used with curing at 160° C to give a wrinkle resistant fabric with useful strength. The combination of glycolic acid and $MgCl_2$ provides such strong catalysis that when used under these treatment conditions, the finished fabric has very poor strength. The strength of the fabric finished with the mixed salt complex as catalyst was 250% greater than the fabric finished with glycolic acid and $MgCl_2$ as catalyst.

EXAMPLE 8

Aqueous solutions of 100 g each were prepared which contained: (a) 9 g of DMDHEU and 2.71 g of PAAO·$H_3PO_4$; (b) 9 g of DMDHEU and 2.60 g of PAAO·$HBF_4$; and (c) 9 g of DMDHEU and 2.73 g of PAAO·$HClO_4$. Swatches of 80×80 cotton printcloth were treated with these solutions by the same procedure as described in Example 4. Results are shown in Table V.

Table V

| Catalyst Used | DP Rating |
|---|---|
| PAAO . $H_3PO_4$ | 3.5 |
| PAAO . $HBF_4$ | 3.3 |
| PAAO . $HClO_4$ | 3.7 |

The DP ratings show that effective catalysis was provided by each of the salts.

EXAMPLE 9

An aqueous solution, 100 g of which contained 9 g of DMDHEU and 2.69 g of PAAO·$CH_3SO_3H$, was used to treat a swatch of 80×80 cotton printcloth by the same procedure as described in Example 4. The treated fabric had a DP rating of 4.0.

This example demonstrates that sulfonic acid salts of PAAO, such as PAAO·$CH_3SO_3H$, are effective catalysts for producing durable press properties in cotton fabric by treatment with methylol amide crosslinking agents.

EXAMPLE 10

Aqueous solutions of 100 g each were prepared which contained 10 g of dimethylol ethyleneurea and (a) 1.05 g of PAAO·HCl; (b) 1.57 g of PAAO·HCl; (c) 2.10 g of PAAO·HCl; or (d) 2.62 g of PAAO·HCl. Swatches of 80×80 cotton printcloth were treated with these solutions by the same procedure as described in Example 4. Results are shown in Table VI.

Table VI

| Catalyst, conc. | Fabric Properties | |
|---|---|---|
| | %N | DP Rating |
| PAAO . HCl, 1.05% | 1.50 | 3.5 |
| PAAO . HCl, 1.57% | 1.56 | 3.7 |
| PAAO . HCl, 2.10% | 1.54 | 3.9 |
| PAAO . HCl, 2.62% | 1.63 | 3.9 |

The example demonstrates that PAAO·HCl is an effective catalyst for producing durable press properties in cotton fabric by treatment with dimethylol ethyleneurea. Further, it shows that the degree of effectiveness of the treatment is a function the catalyst concentration with a wide range of catalyst concentrations being operable.

EXAMPLE 11

Aqueous solutions of 100 g each were prepared which contained 2.63 g of PAAO·oxalic acid and (a) 10 g of dimethylol methyl carbamate; (b) 12.5 g of trimethylol melamine; or (c) 15 g of methylated urea-formaldehyde Swatches of 80×80 cotton printcloth were treated with these solutions by the same procedure described in Example 4. Results are shown in Table VII.

Table VII

| Methylol Amide Crosslinking Agent Used | DP Rating |
| --- | --- |
| Dimethylol methyl carbamate | 3.9 |
| Trimethylol melamine | 3.3 |
| Methylated urea-formaldehyde | 4.3 |

This example demonstrates that the catalysts of this invention are effective in producing improved durable press properties in cotton fabrics by treatments with carbamate, melamine, and urea-type methylol amide crosslinking agents.

EXAMPLE 12

An aqueous solution was prepared which contained, by weight, 10% dimethylol ethyleneurea and 2.1% PAAO·HCl. Swatches of a 50/50 polyester/cotton sheeting and of a 65/35 polyester/cotton broadcloth were treated with this solution by the procedure described in Example 4. Results are shown in Table VIII.

Table VIII

| Fabric type, polyester/cotton content | DP Rating Untreated | DP Rating Treated |
| --- | --- | --- |
| Sheeting, 50/50 | 3.3 | 4.0 |
| Broadcloth, 65/35 | 2.6 | 4.3 |

This example demonstrates that the catalysts of this invention are effective in producing improved durable press properties in treatments carried out on fabrics of various fabric types and polyester/cotton fiber compositions.

EXAMPLE 13

An aqueous solution was prepared which contained, by weight, 15% dimethylol ethyleneurea and 3.14% PAAO·HCl. A swatch of 35/65 polyester/rayon twill was treated with the solution by the procedure described in Example 4. Durable press rating of the treated fabric was 3.6 compared with a rating of 2.7 for the untreated fabric.

This example demonstrates that the catalysts of this invention are useful in producing improved durable press properties in treatments of fabrics in which the cellulose component is rayon.

We claim:

1. In a method of preparing wrinkle resistant textile fabrics that are composed of at least 35 weight percent of a cellulosic fiber wherein said textile materials are:
   a. impregnated with an aqueous solution comprised of 5 to 20% by weight of a methylol amide crosslinking agent and a catalyst; and
   b. dried and cured, the improvement wherein the catalyst is contained in said aqueous solution in amounts equal to 0.2% to 6% by weight and is selected from the group consisting of salts of 1,3,5-triaza-7-phosphaadamantane and inorganic, organic, and sulfonic acids, salts of 1,3,5-triaza-7-phosphaadamantane-7-oxide and inorganic, organic, and sulfonic acids, and mixed salt complexes of 1,3,5-triaza-7-phosphaadamantane, an organic acid, and an inorganic salt.

2. A process for the treatment of textile materials that are composed of at least 35 weight percent of a cellulosic fiber to produce textile materials with improved wrinkle resistance and durable press properties which process comprises:
   a. impregnating a cellulose-containing textile material by immersing it in an aqueous treatment solution containing 5 to 20% by weight of a methylol amide crosslinking agent with about 0.2 to 6% by weight of a catalyst selected from the group consisting of salts of 1,3,5-triaza-7-phosphaadamantane and inorganic, organic, and sulfonic acids, salts of 1,3,5-triaza-7-phosphaadamantane-7-oxide and inorganic, organic, and sulfonic acids, and mixed salt complexes of 1,3,5-triaza-7-phosphaadamantane, an organic acid, and an inorganic salt;
   b. squeezing the impregnated textile material free of excess treatment solution;
   c. drying the textile from (b) at a temperature so that the temperature of the textile does not exceed about 100° C; and
   d. curing the textile from (c) at a temperature of about 140°–200° C from about 15 seconds to about 3 minutes, time and temperature being inversely adjusted.

* * * * *